United States Patent
Conti et al.

(10) Patent No.: US 11,065,349 B2
(45) Date of Patent: Jul. 20, 2021

(54) 18F LABELED BODIPY DYE AND ITS DERIVATIVES FOR PET IMAGING OF HEART PERFUSION AND OTHERS

(71) Applicants: Peter S. Conti, Pasadena, CA (US); Zibo Li, Logan, UT (US); Shuanglong Liu, Alhambra, CA (US); Dan Li, Los Angeles, CA (US)

(72) Inventors: Peter S. Conti, Pasadena, CA (US); Zibo Li, Logan, UT (US); Shuanglong Liu, Alhambra, CA (US); Dan Li, Los Angeles, CA (US)

( * ) Notice: Subject to any disclaimer, the term of this patent is extended or adjusted under 35 U.S.C. 154(b) by 508 days.

(21) Appl. No.: 14/438,863

(22) PCT Filed: Mar. 15, 2013

(86) PCT No.: PCT/US2013/032631
§ 371 (c)(1),
(2) Date: Apr. 27, 2015

(87) PCT Pub. No.: WO2014/065874
PCT Pub. Date: May 1, 2014

(65) Prior Publication Data
US 2015/0297760 A1    Oct. 22, 2015

Related U.S. Application Data

(60) Provisional application No. 61/719,212, filed on Oct. 26, 2012.

(51) Int. Cl.
*A61K 51/04*     (2006.01)
*A61K 49/00*     (2006.01)
*A61B 5/00*      (2006.01)
*A61B 6/03*      (2006.01)

(52) U.S. Cl.
CPC ........ *A61K 51/0446* (2013.01); *A61B 5/0035* (2013.01); *A61B 5/0071* (2013.01); *A61B 6/032* (2013.01); *A61B 6/037* (2013.01); *A61K 49/0002* (2013.01); *A61K 49/0021* (2013.01)

(58) Field of Classification Search
CPC ......... A61K 51/04; A61K 49/00; A61B 6/032
See application file for complete search history.

(56) References Cited

U.S. PATENT DOCUMENTS

2013/0189185 A1*  7/2013  Li ..................... A61K 49/0002
                                                    424/1.65

OTHER PUBLICATIONS

Todd W. Hudnall et al., A BODIPY boronium cation for the sensing of fluoride ions, Chem. Commun, 4596-4597 (Year: 2008).*
Zibo Li et al., Rapid aqueous [18F]—labeling of a bodipy dye for positron emission tomography/fluorescence dual modality imaging, Chem. Commun, 47, 9324-9326 (Year: 2011).*
J. Adam Hendricks et al., Synthesis of [18F]BODIPY: Bifunctional Recporter for Hybrid Optical/Positron Emission Tomography Imaging, Angew Chemie, 51, 4603-4606. (Year: 2012).*
International Preliminary Report on Patentability dated Apr. 28, 2015 issued in corresponding PCT application PCT/US2013/032631.

* cited by examiner

Primary Examiner — Michael G. Hartley
Assistant Examiner — Jagadishwar R Samala
(74) Attorney, Agent, or Firm — DLA Piper LLP (US)

(57) ABSTRACT

This invention provides a class of dual mode imaging tracer capable of acting both as a fluorescent imaging tracer and a positron emission tomography imaging tracer. Tracers in accordance with this invention generally have a fluorescent core with a boron-fluoride element embedded therein. Exemplary embodiments of the tracer include $^{18}$F-labeled BODIPY compounds and derivative thereof. Also provided are tracer kits containing a sterile formulation of a BODIPY dye either in a radio-labeled or pre-labeled state, and methods for imaging heart perfusion using the $^{18}$F-labeled dual mode tracers.

4 Claims, 6 Drawing Sheets

18F LABELED BODIPY DYE AND ITS DERIVATIVES FOR PET IMAGING OF HEART PERFUSION AND OTHERS

CROSS-REFERENCE TO RELATED APPLICATIONS

This application is a national stage of international application number PCT/US2013/032631, filed on Mar. 15, 2013, which claims the benefit of Provisional Application No. 61/719,212 filed Oct. 26, 2012, the entire content of all of which are hereby incorporated herein by reference.

FIELD OF THE INVENTION

The present invention relates generally to the field of myocardial perfusion imaging (MPI). More particularly, the present invention relates to the use of $^{18}$F labeled BODIPY dye as a new class of imaging probe for positron emission tomography (PET) MPI.

BACKGROUND OF THE INVENTION

Coronary artery disease and its related cardiac disorders represent the most common cause of death in the USA and Western world. Although recent advancements in treatment have led to improved patient outcomes and survival prospects, correctly diagnosing and assigning a patient's candidacy for the most effective therapy option is the critical success factor in benefiting from these advancements (1, 2). To this end, myocardial perfusion imaging (MPI) has demonstrated excellent diagnostic accuracy, superb ability to perform risk stratification, and capability for demonstrating therapeutic benefit when applied in the management of the cardiac patient (1-5).

MPI is a nuclear medicine procedure that illustrates the function of the heart muscle (myocardium). It evaluates many heart conditions from coronary artery diseases to hypertrophic cardiomyopathy and myocardial wall motion abnormalities. The function of the myocardium is also evaluated by calculating the left ventricular ejection fraction of the heart. This scan is done in conjunction with a cardiac stress test. While a myocardial perfusion scan can determine with significant accuracy whether a patient has two or fewer coronary arteries which are dangerously occluded, the scan has a major inherent fault in accuracy which inevitably results in missed diagnoses of persons who suffer from three-vessel disease, the most serious form of coronary artery occlusion. In simple terms, patients who have all their major arteries occluded will not be readily distinguishable from healthy subjects since there will be no un-occluded arteries to compare with. In other words, while MPI can accurately diagnose patients with 1 or 2 arterial blockages, it will miss the most serious cases with all three arteries occluded.

Recently, MPI advanced further with the addition of hybrid PET/CT and SPECT/CT systems. For example, cardiac PET-CT imaging is advancing the ability to image the structure and function of the heart and vasculature by providing concurrent quantitative information about myocardial perfusion and metabolism with coronary and cardiac anatomy. Precise measurement of regional blood flow has significant clinical importance in identifying ischemia, defining the extent and severity of disease, assessing myocardial viability, establishing the need for medical and surgical intervention, and monitoring the effects of treatments (6, 7).

Positron emission tomography (PET) is a nuclear medicine imaging technique that produces a three-dimensional image or picture of functional process in the body. The system detects pairs of gamma rays emitted indirectly by a positron-emitting radionuclide (tracer) which is introduced into the body on a biologically active molecule. Three-dimensional images of tracer concentration within the body are then constructed by computer analysis. In modern scanners, three-dimensional imaging is often accomplished with the aid of a CT X-ray scan (PET-CT) performed on the patient during the same session, in the same machine.

For myocardial perfusion PET-CT imaging, the positron-emitting radiopharmaceutical must be taken up into the myocardium in proportion to blood flow in order to evaluate areas with reduced blood flow (for example due to ischemia). Several tracers have been used for evaluating myocardial perfusion with PET in clinical practice, including $^{82}$Rb chloride, $^{15}$O-water, and $^{13}$N-ammonia. The short physical half-life of these isotopes allows rapid sequential imaging of rest and stress perfusion.

There are several advantages to evaluating coronary artery diseases (CAD) with PET. CAD is a complex, dynamic disease and quantitative measurements of myocardial blood flow by PET can improve the functional characterization of CAD. The major advantage of PET over SPECT is its ability to provide attenuation-corrected images, which decreases incidence of attenuation artifacts and increases specificity. MPI with PET can also provide more accurate information on localization of diseases, as well as quantitative assessment, in absolute values, of myocardial blood flow. The measurement of regional flow reserve allows for physiologic characterization of stenosis severity, and may provide early detection of CAD as well as prognosis information.

Despite the potential advantages of MPI PET, there are still certain critical difficulties associated with the technique. In particular, the toxicity of the radioactive tracers is a major concern. Additionally, finding a suitable probing molecule that can reach the desired anatomical location, easy to label, inexpensive to produce, and has low risk of physiological side-effects such as allergic reactions is not an easy task. Currently available tracers are limited in range and all have their problems.

For example, the short half-life of most positron emitting isotopes (from 1-10 min) significantly limits the duration and timing of imaging. Because of this limitation, the tracers usually have to be produced using a cyclotron in close proximity to the PET imaging facility, placing a significant limitation on facility deployment. Commercial distribution of such agents is also similarly limited, and their associated production costs can be very high.

In view of the above, there still exists a great unmet need for an inexpensive, long lasting, safe PET MPI tracer that has good biodistribution profile.

SUMMARY OF THE INVENTION

As explained above, new tracers with long half-lives and excellent biodistribution profiles are the key to advancing applications of PET MPI. To this end, several $^{18}$F and $^{64}$Cu labeled tracers are currently being actively investigated as probes for myocardial PET imaging (8-14). For example, $^{18}$F-flurpiridaz (also known as $^{18}$F-BMS747158-02), $^{18}$F-fluorobenzyltriphenylphosphonium ($^{18}$F-FBnTP), and $^{18}$F-rhodamines have shown great potential for PET MPI (8-12).

These novel MPI agents holds potential to complement currently used $^{13}$N—NH$_3$ and $^{82}$Rb to advance the state of the art in PET MPI imaging.

In this invention, we have unexpectedly discovered that $^{18}$F-BODIPY can function exceptionally well as an imaging tracer for PET MPI. In particular, we demonstrate for the first time the biodistribution and in vivo imaging of the readily available $^{18}$F-labeled BODIPY dye. This discovery opens up a new category of cationic tracer agents for PET MPI, herein referred to as dual mode tracers.

Accordingly, one aspect of the present invention is directed to novel $^{18}$F-labeled compounds and their uses as dual mode PET tracers.

Dual mode tracers of the present invention will generally have a fluorescent core with a boron-fluoride element embedded. In a preferred embodiment, dual mode tracers are $^{18}$F-labeled BODIPY compounds. As used herein, the term "BODIPY" refers to the class of boron-dipyrromethene compound having the general formula:

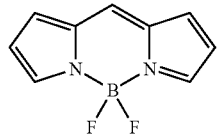

wherein the core can have a variety of substitution. Because the BODIPY core is also a fluorophore, $^{18}$F-labeled BODIPY tracers are actually dual mode tracers that can simultaneously provide integrated imaging information in both PET imaging and fluorescent imaging.

Table 1 shows a range of other exemplary dual mode tracers in accordance with embodiments of the present invention.

In a preferred embodiment, the $^{18}$F-labeled BODIPY compound is one having the formula:

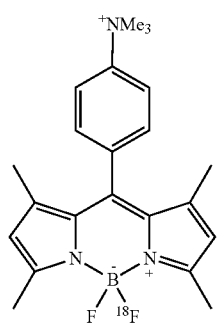

Because BODIPY compounds do not have any specific targeting feature, it was not known how they would be distributed in vivo. In this invention, the inventors have unexpectedly discovered that BODIPY have excellent biodistribution profile suitable for myocardial perfusion imaging. Accordingly, another aspect of the present invention is directed to a method of performing PET MPI using one or more $^{18}$F-labeled BODIPY compounds as the tracers.

Methods in accordance with this aspect of the invention will generally include the steps of administering to a subject an effective amount of a $^{18}$F-labeled BODIPY compound or a composition comprising an effective amount of a $^{18}$F-labeled compound by injection, infusion, or any other known method; and imaging the area of the patient wherein the event of interest is located, preferably the heart, using a suitable imaging technique, wherein said suitable imaging techniques is selected from the group consisting of PET, PET-CT, fluorescent imaging, and combinations thereof.

The useful dosage to be administered and the particular mode of administration will vary depending upon such factors as age, weight, and particular region to be treated, as well as the particular contrast agent used, the diagnostic use contemplated, and the form of the formulation, for example, suspension, emulsion, microsphere, liposome, or the like, as will be readily apparent to those skilled in the art.

Another aspect of the present disclosure is diagnostic kits for the preparation of diagnostic agents for detecting, imaging, and/or monitoring myocardial perfusion. Diagnostic kits of the present disclosure comprise one or more containers containing a composition(s) of the sterile, non-pyrogenic, formulation comprising a predetermined amount of a reagent of the present disclosure, and optionally other components such as one or two ancillary ligands such as tricine and 3-[bis(3-sulfophenyl)phosphine]benzenesulfonic acid (TPPTS), reducing agents, transfer ligands, buffers, lyophilization aids, stabilization aids, solubilization aids and bacteriostats; and an instruction for forming and administering a tracer using the composition(s) in the containers. The kits may also comprise a reducing agent, such as, for example, tin(II).

Unless otherwise defined, all technical and scientific terms used herein have the same meaning as commonly understood by one of ordinary skill in the art to which this invention pertains. In case of conflict, the present document, including definitions, will control. All publications, patent applications, patents and other references mentioned herein are incorporated by reference in their entirety. The materials, methods, and examples disclosed herein are illustrative only and not intended to be limiting. Other features, objects, and advantages of the invention will be apparent from the attached description and the accompanying drawings, and from the appended claims.

DETAILED DESCRIPTION

Definition

Figure 1:
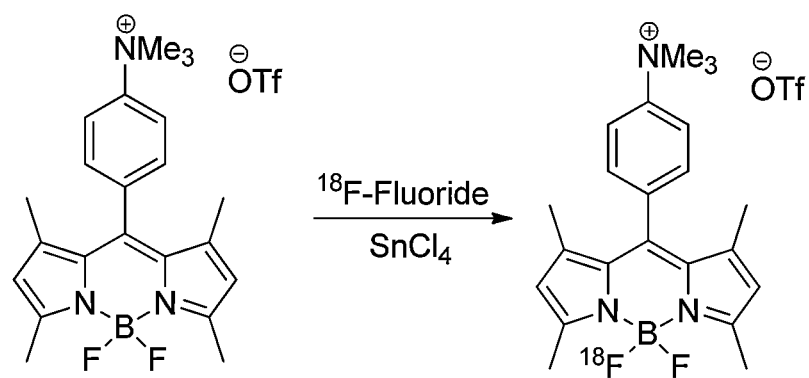
FIG. 1 shows an exemplary synthetic scheme of $^{18}$F-BODIPY-1.

Unless otherwise indicated herein, all terms used herein have the meanings that the terms would have to those skilled in the art of the present invention. Practitioners are particularly directed to current textbooks for definitions and terms of the art. It is to be understood, however, that this invention is not limited to the particular methodology, protocols, and reagents described, as these may vary.

The term "alkyl" herein used means $C_1$-$C_{10}$ straight or branched chain alkyl or cycloalkyl, for example, methyl, ethyl, n-propyl, i-propyl, n-butyl, i-butyl, sec-butyl, tert-butyl, n-pentyl, i-pentyl, neo-pentyl, tert-pentyl, and the like.

Substituents for an optionally substituted alkyl include hydroxy, alkoxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkoxycarbonyl (e.g., methoxycarbonyl and ethoxycarbonyl), nitro, cyano, haloalkyl (e.g., trifluoromethyl), substituted or unsubstituted amino (e.g., methylamino, dimethylamino, and carbamoylamino), guanidino, phenyl, benzyloxy, and the like. These substituents are able to bind them at one or more of any possible positions.

The term "aryl" herein used means monocyclic or condensed ring aromatic hydrocarbons. Examples of the aryl are phenyl, naphthyl, and the like.

Substituents for the aromatic ring of in an optionally substituted aryl are, for example, hydroxy, alkoxy, alkyl, halogen, carboxy, alkoxycarbonyl, nitro, cyano, haloalkyl, aryloxy, substituted or unsubstituted amino. These substituents are able to bind to it at one or more of any possible position.

The term "carboxylic acid" means an organic chemical compound comprising at least one carboxylic acid functional group (i.e. —C(O)OH).

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

Integrated PET-CT has been widely applied in clinical care as a novel diagnostic imaging tool in patient management owing to its high sensitivity and good resolution. Recently, application of PET-CT has been extended to cardiovascular-related diseases and is undergoing rapid expansion in this area (6, 23-24). These systems permit the integration of the presence of coronary artery calcium and the degree of coronary artery luminal narrowing with the impairment in myocardial vasodilator function. To date, a number of PET MPI probes have been developed for clinical applications. However, many of the tracers may require expensive onsite production and inconvenient on-scanner tracer administration. Currently, there is considerable interest in developing novel PET MPI agents with optimal imaging property and longer radioactive half-lives than conventional agents.

BODIPY dyes constitute a class of fluorophores that have been widely used for the fluorescent labeling of biomolecules (25-27). Such dyes feature high stability, high quantum yields and an emission range that can be tuned into the near infrared (28-29). BODIPY dyes also typically possess a boron-bound fluorine atom which could provide a site for the incorporation of a [$^{18}$F]-fluorine atom, a radionuclide of choice for PET (25-27). In fact, we have discovered the novel methods to produce $^{18}$F-BODIPY dyes in high yield. As the reported BODIPYs may be considered as lipophilic cationic compounds, they may move across phospholipid bilayers similar to the well-studied triphenylphosphonium (TPP) ion (30-31). It has long been recognized that lipophilic cations such as TPP$^+$ and the fluorescent dye rhodamine derivatives have an affinity to, and accumulate selectively in, the mitochondrial matrix. However, it is heretofore unknown whether BODIPY or similar dyes will have the desired properties suitable for myocardial perfusion imaging.

In this invention, we unexpectedly discovered that BODIPY dyes preferentially accumulate in the heart. We previously disclosed novel methods for efficiently synthesizing and purifying large quantities of $^{18}$F labeled BODIPY dyes in co-pending application Ser. No. 13/549,309, the entire content of which is incorporated herein by reference. Using the $^{18}$F-BODIPY-1 probe in bio-distribution study and microPET imaging experiments, we demonstrated for the first time the preferential accumulation of such dyes in the heart in mice. In the microPET study, the heart uptake of $^{18}$F-BODIPY-1 was calculated to be 4.38±0.46, 3.51±0.42, and 2.68±0.17% ID/g at 0.5, 2 and 3 h p.i. This demonstrated that $^{18}$F-BODIPY-1 preferentially accumulated in the heart. Similarly, rat images indicate rapid blood clearance and clear delineation of the plateau of heart activity for the scanning period. As the rat is much larger than mouse, the uptakes derived from rat imaging are expected to be more accurate than the one from mouse.

With the above discoveries, we have uncovered a new class of dual mode tracer for PET imaging in MPI imaging applications. As BODIPY dyes provide various positions to be modified, those skilled in the art will readily recognize that various modifications may be made to achieve different hydrophilicity and zeta potentials. Such modifications can be guided by side-by-side comparisons with currently available compounds.

In summary, we have discovered a new category of cationic compounds that hold great potential for dual mode imaging (fluorescent and PET) in imaging applications such as myocardial perfusion imaging.

EXAMPLES

The following examples are provided in order to demonstrate and further illustrate certain embodiments and aspects of the present invention and are not to be construed as limiting the scope thereof. While such examples are typical of those that might be used, other procedures known to those skilled in the art may alternatively be utilized. Indeed, those of ordinary skill in the art can readily envision and produce further embodiments, based on the teachings herein, without undue experimentation.

Material and Methods

All chemicals obtained commercially were of analytical grade and used without further purification. No-carrier-added $^{18}$F—F$^-$ was obtained from in-house a Siemens RDS-112 negative ion cyclotron. The analytical reversed-phase high performance liquid chromatography (RP-HPLC) using a Vydac protein and peptide column (218TP510; 5 μm, 250×4.6 mm) was performed on a Dionex 680 chromatography system with a UVD 170U absorbance detector and model 105S single-channel radiation detector (Carroll & Ramsey Associates). The recorded data were processed using Chromeleon version 7.1 software. With a flow rate of 1.0 mL/min, the mobile phase was changed from 95% solvent A [0.1% trifluoroacetic acid (TFA) in water] and 5% B [0.1% TFA in acetonitrile (MeCN)] (0-2 min) to 5% solvent A and 95% solvent B at 22 min. UV absorbance was monitored at 218 nm and the identification of the peptides were confirmed based on the UV spectrum using a photo-diode array detector.

Preparation of $^{18}$F-Labeled BODIPY Dyes $^{18}$F-BODIPY-1 was synthesized according to our previously reported procedure (16). In brief, approximately 30 mCi azeotropically dried $^{18}$F-fluoride in anhydrous MeCN was added to the mixture of BODIPY-1 (0.37 μmol) and SnCl$_4$ (1 μl) in 50 μl MeCN. The reaction mixture was incubated for 10 min at room temperature. Then approximately 1.5 mCi mixture was taken for HPLC purification. The purified radio tracer was rotary evaporated to dryness, reconstituted in normal saline and passed through a 0.22-μm Millipore filter into a sterile multidose vial for in vitro and in vivo experiments.

Animal Models

Animal procedures were performed according to a protocol approved by the Institutional Animal Care and Use Committee (IACUC) of University of Southern California. 4-6 weeks old female athymic nude mice (BALB/c nu/nu) and 2-3 weeks old male rats were purchased from Harlan Laboratories (Indianapolis, Ind.). The animals were housed in our vivarium for 4 weeks before use.

Cell Culture and Fluorescence-Activated Cell Sorting (FACS) Analysis

Human embryonic kidney 293 (HEK-293) cells were culture in RPMI-1640 (containing 5.3 mM KCl) and 10% fetal bovine serum (Omega Scientific, Tarzana, Calif.). HEK-293 cells were harvested by trypsinization and aliquoted to 1×10$^6$ cells/tube. Cells were suspended in 200 μL medium containing different concentration of Bodipy-1 (6.25 μM, 12.5 μM, 25 μM or 50 μM) and KCl (5.3 mM, 100 mM or 200 mM). Then the cells were maintained in cell incubator for 1.5 h. After incubation, cells were washed twice with cold phosphate-buffered saline (PBS) and stained with 100 μl 4'-6-diamidino-2-phenylindole (DAPI, 1 μg/ml) diluted in PBS. For the quantification of fluorescence by flow cytometry (CyAn analyzer, Beckman Coulter), 10,000 viable cells (DAPI negative) were counted and analyzed. The excitation and emission wavelength were 488 nm and 510-550 nm respectively. Each sample was repeated as triplicate.

In Vitro Uptake Assay

HEK-293 (1×10$^6$) cells were suspended in 200 μl medium containing different concentration of KCl (5.3 mM, 100 mM or 200 mM) and 1 μCi $^{18}$F-BODIPY-1 was added. Then the cells were maintained in cell incubator for 1.5 h. After incubation, cells were washed twice with cold phosphate-buffered saline (PBS). The radioactivity of the cell pellet was counted together with standard solution in a gamma counter. The data were obtained in triplicate.

microPET Imaging Studies

PET scans and image analysis were performed using a microPET R4 rodent model scanner (Siemens Medical Solutions) as previously reported (17-18). $^{18}$F-BODIPY-1 was intravenously injected into nude mice (approximately 100 μCi each, n=3) and rats (approximately 500 μCi each, n=3) under isoflurane anesthesia. Five min static PET images were then acquired for each scan. The images were reconstructed by 2-dimensional ordered-subsets expectation maximum (OSEM) algorithm. No attenuation or scatter correction was applied. For each microPET scan, regions of interest (ROIs) were drawn over the normal tissue, and major organs by using vendor software (ASI Pro 5.2.4.0) on decay-corrected whole-body coronal images. The average radioactivity concentration (accumulation) within an organ was obtained from mean pixel values within the multiple ROI volume, which were converted to counts/mL/min by using a conversion factor. Assuming a tissue density of 1 g/mL, the ROIs were converted to counts/g/min and then divided by the administered activity to obtain an imaging ROI-derived % ID/g.

Biodistribution Study of $^{18}$F-BODIPY-1

The health nude mice were intravenously injected with approximate 50 μCi of $^{18}$F-BODIPY-1. At 3 h after injection, the mouse was sacrificed, then the blood, heart and other major organs were collected, and wet-weighed. The radioactivity in the tissue was measured using a γ counter (Packard, Meriden, Conn.). The results are presented as percentage injected dose per gram of tissue (% ID/g). Values are expressed as means±SD for a group of three animals.

Fluorescence Microscope Analysis

HEK-293 cells were planted in 24-well plate at density 1×10$^5$ cells/well. 24 h after plantation, cells were incubated with 300 μl medium containing 25 mM BODIPY-1 and different concentration of KCl (5.3 mM or 150 mM). Then the cells were maintained in cell incubator for 1.5 h. After incubation, cells were washed twice with cold phosphate-buffered saline (PBS), fixed with 4% paraformaldehyde (Electron Microscopy Sciences, Hatfield, Pa.) and stained with DAPI. Images were obtained with Nikon Eclipse 80i fluorescence microscope (Tokyo, Japan).

Statistical Analysis

Quantitative data was expressed as mean±SD. Means were compared using one-way ANOVA and student's t-test. P values of <0.05 were considered statistically significant.

Results

Radiochemistry

The one-step $^{18}$F-fluorination of BODIPY-1 afforded $^{18}$F-BODIPY-1 in 89.67±3.21% yield (n=4) (FIG. 1). Counted from the end of bombardment, the total synthesis included HPLC purification and product formulation was 62.33±7.51 min (n=4). The specific activity (SA) to $^{18}$F-BODIPY-1 was estimated to be 48 mCi/μmol at the time of injection based on the chemical loading and the radiochemical yield (RCY).

Cell Uptake Study

Figure 6:
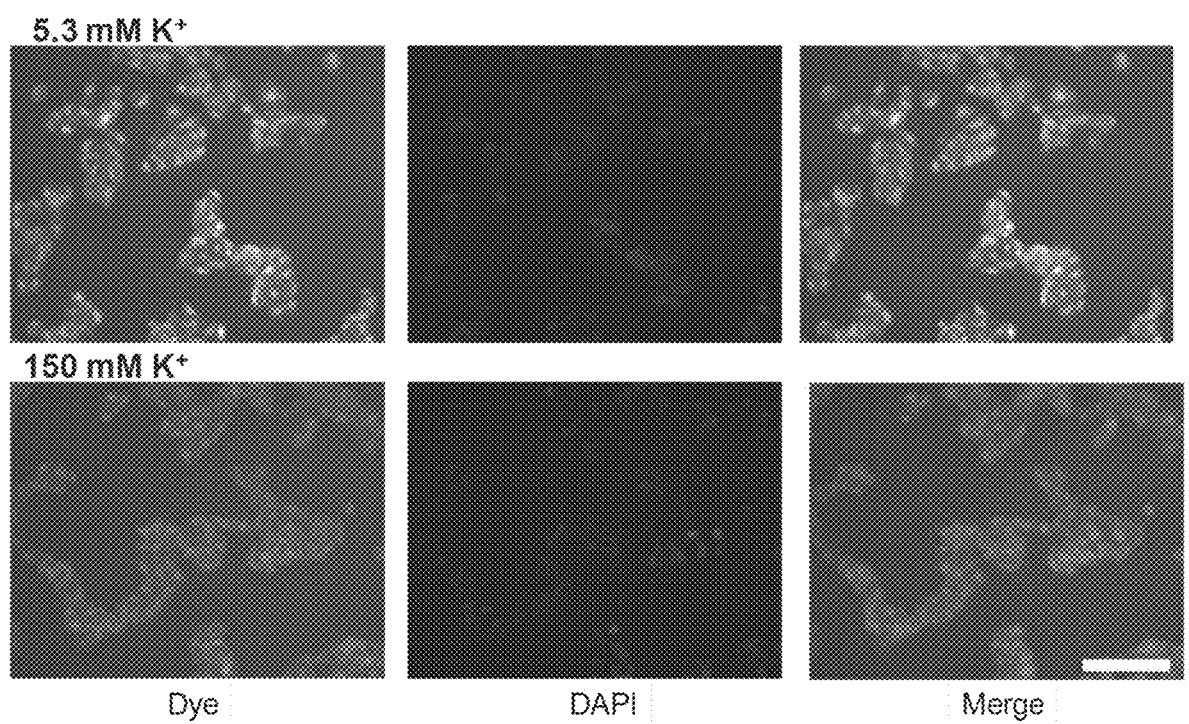
FIG. 6 The observation of BODIPY-1 uptake in HEK-293 cell after incubation at standard solution (top) and high potassium solution (bottom).

HEK-293 cell uptake of BODIPY-1 was assessed through FACS analysis. The mean fluorescence intensity of cells was elevated with the increase of BODIPY-1 concentration (FIG. 2A). For testing the potassium concentration effect, the relative mean fluorescence intensity of HEK-293 cells in 5.3 mM $K^+$ (25 μM BODIPY-1) was set as 1 and the other fluorescence intensity was expressed as the ratios to 5.3 mM $K^+$. With the increasing of potassium concentration, the corresponding fluorescence intensity was dropped to 0.69±0.06 in 100 mM $K^+$ and 0.39±0.01 in 200 mM $K^+$ solution (FIG. 2B). Fluorescence microscope analysis also showed the decrease of cell fluorescence intensity in 150 mM $K^+$ compared to 5.3 mM $K^+$ (FIG. 6).

Figure 2:
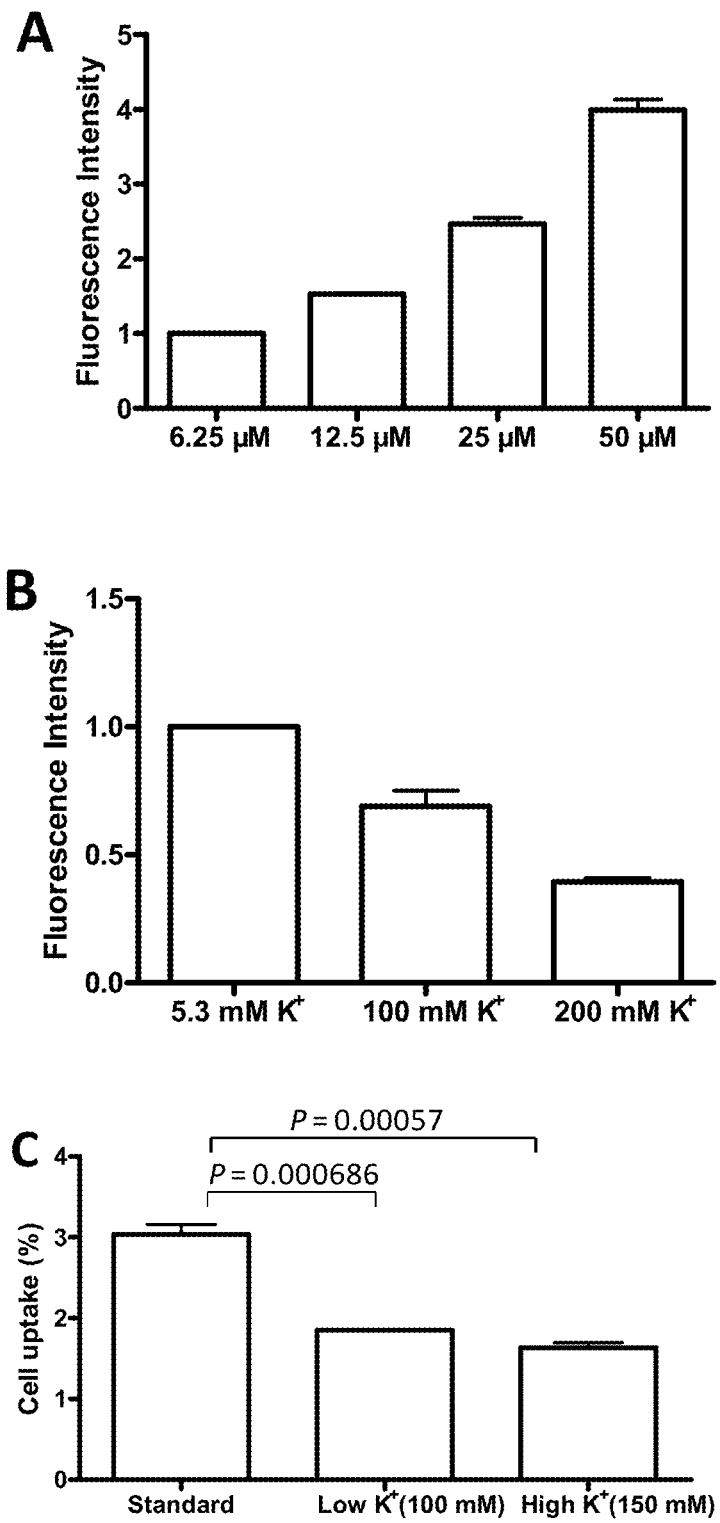
FIG. 2 (A) FACS analysis of HEK-293 cell uptake with different BODIPY-1 concentrations after incubation 37° C. for 1.5 h. 6.25 μM BODIPY-1 as reference for all the calculation. (B) FACS analysis of HEK-293 cell uptake with different potassium concentrations after incubation HEK-293 cell with 25 μM BODIPY-1 at 37° C. for 1.5 h. Values achieved with standard solution were used as reference for all the calculation. (C) Cell uptake study on the different K$^+$ concentration after incubation HEK-293 cell with 25 μM $^{18}$F-BODIPY-1 at 37° C. for 1.5 h. Values are all expressed as mean percentage of normalized uptake±SD of 3 independent experiments.

Similarly, the effects of manipulating mitochondrial membrane potential on cellular accumulation of $^{18}$F-BODIPY-1 were assessed through uptake studies on HEK-293 cells using 2 potassium concentration (medium $K^+$, 100 mM and high $K^+$, 200 mM). For control experiments, in which the mitochondrial membrane potentials were unaltered, uptake was determined in a near-physiologic buffer (standard solution, $K^+$ concentration: 5.3 mM). The results are depicted in FIG. 2. The HEK-293 cell uptake of $^{18}$F-BODIPY-1 in standard solution was 2.96±0.24% while the cell uptake in medium $K^+$ and high $K^+$ solution were 1.85±0.01% and 1.62±0.16%, respectively (FIG. 2). These results clearly demonstrated that uptake of $^{18}$F-BODIPY-1 was electrogenic and driven by the plasma and mitochondrial membrane potentials.

Fluorescence Microscope Analysis

HEK-293 cells were incubated with medium containing 25 mM BODIPY-1 and different concentration of KCl (5.3 mM or 150 mM). Then the cells were maintained in cell incubator for 1.5 h. Fluorescence microscope analysis showed the decrease of cell fluorescence intensity in 150 mM $K^+$ compared to 5.3 mM $K^+$.

microPET Imaging of Normal Mice and Rats

Figure 3:
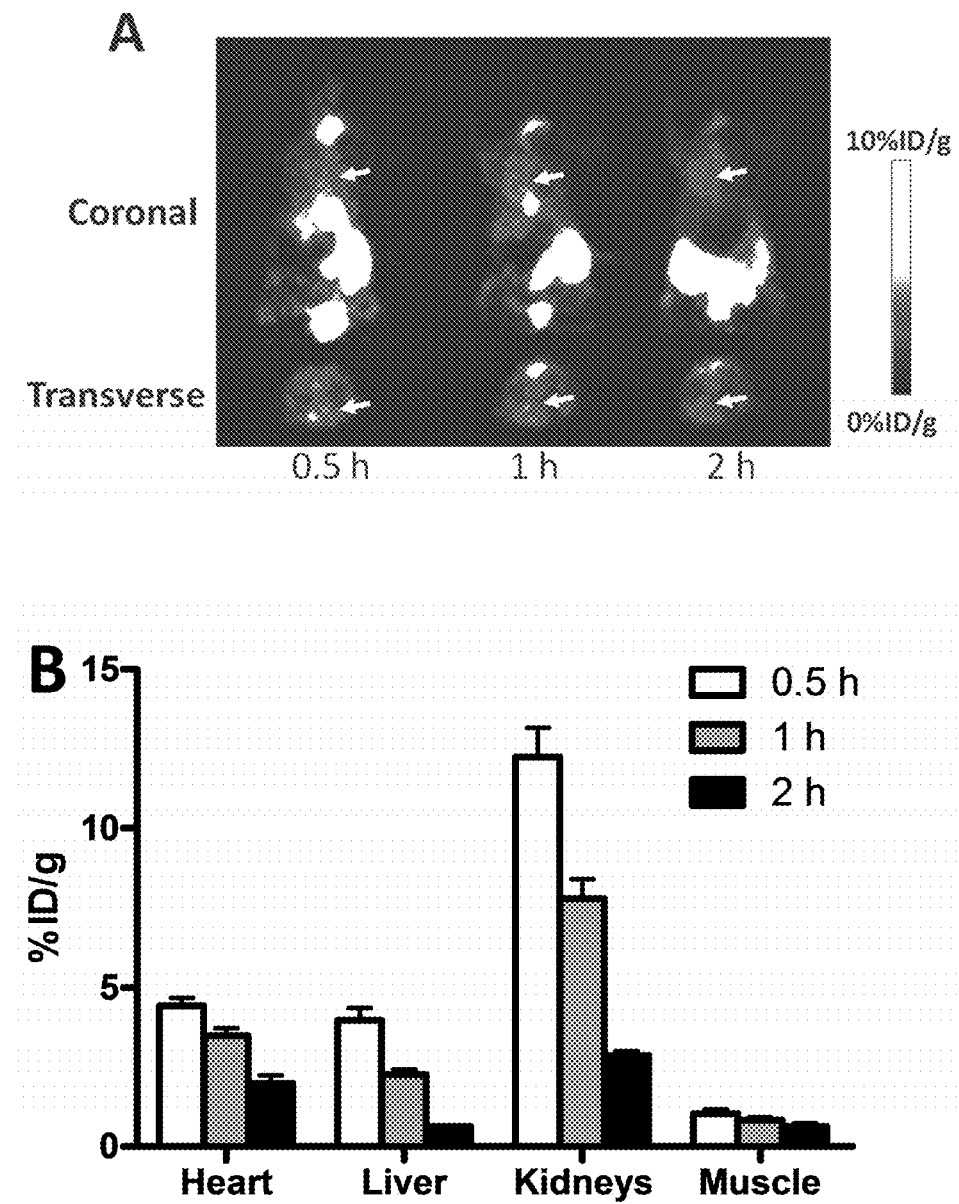
FIG. 3 (A) Decay-corrected wholebody coronal and transverse microPET images of athymic female nude mice at 0.5, 2, and 3 h after injection of $^{18}$F-BODIPY-1 (100 μCi). Images shown are 5 min static scans of a single mouse, but is representative for the 3 mice tested in each group. Hearts are indicated by arrows. (B) microPET quantification by measuring the ROIs.

Statistic microPET scans were performed on health female nude mice (n=3) (19-22) and selected coronal images at different time points after injection of $^{18}$F-BODIPY-1 were shown in FIG. 3A. The heart was clearly visible at each time point examined. Quantification of major organ activity accumulation in microPET scans was realized by measuring ROIs encompassing the entire organ in the coronal orientation. The averaged time-activity curves (TACs) of $^{18}$F-BODIPY-1 in heart, liver, kidneys, and muscle were shown in FIG. 3B. The heart uptake of $^{18}$F-BODIPY-1 was calculated to be 4.43±0.44, 3.49±0.40, and 1.98±0.45% ID/g at 0.5, 1 and 2 h p.i. $^{18}$F-BODIPY-1 showed substantially high kidney uptake at 0.5 h p.i. (12.26±1.57% ID/g). The fast clearance of $^{18}$F-BODIPY-1 gave significantly lower kidney uptake at 2 h p.i., which are 2.86±0.24% ID/g, respectively. Therefore, the fast clearance and high binding to heart tissue of $^{18}$F-BODIPY-1 gave high contrasts. For example, the heart-to-liver and heart-to-muscle reached 3.13±0.39, and 3.16±0.30 at 2 h p.i., respectively.

Figure 4:
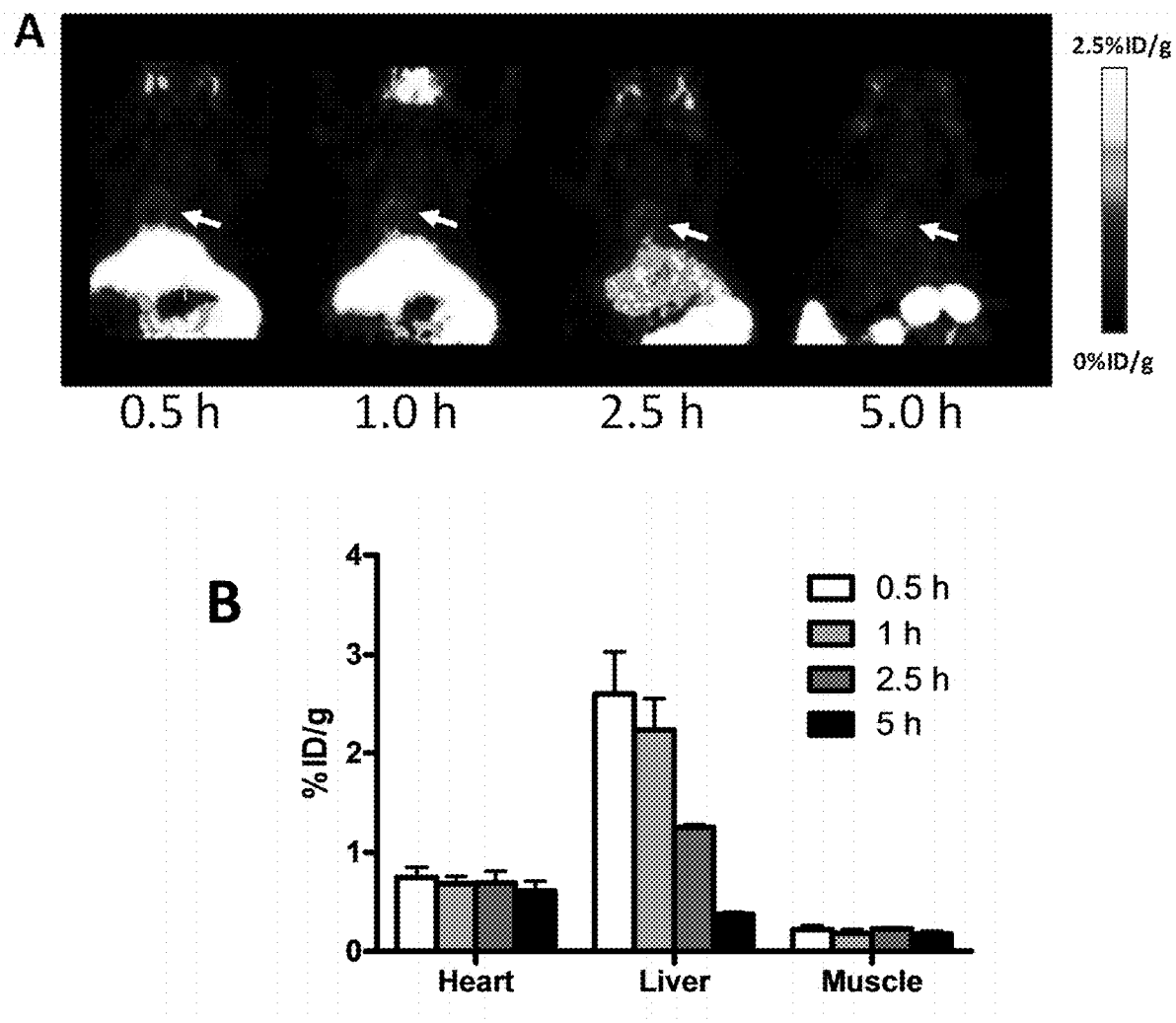
FIG. 4 (A) Decay-corrected chest region coronal microPET images of rats at 0.5, 1, 2.5 and 5 h after injection of $^{18}$F-BODIPY-1 (200 μCi). Images shown are 5 min static scans of a single rat, but is representative for the 3 rats tested in each group. Hearts are indicated by arrows. (B) microPET quantification by measuring the ROIs.

Statistic microPET scans were also performed on health rats (n=3) and selected coronal images at different time points after injection of $^{18}$F-BODIPY-1 were shown in FIG. 4A. Heart could be also clearly visualized at all time-points examined. Due to the larger size of rats, the heart of uptake are consistently lower than those in mouse study, which are 0.75±0.14, 0.69±0.10, 0.70±0.16, and 0.61±0.14% ID/g at 0.5, 1, 2.5 and 5 h p.i. However, the contrasts are consistent with those in the mouse study. For example, the heart to muscle ratios is 3.07±0.49 at 2.5 h p.i.

Bio-Distribution Study of $^{18}$F-BODIPY-1 in Mouse

Figure 5:
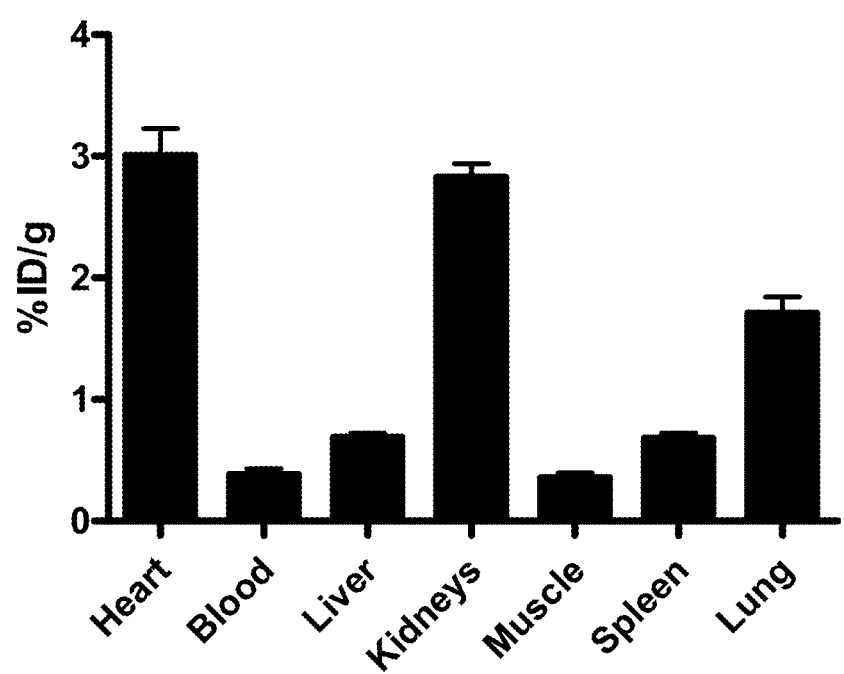
FIG. 5 Biodistribution studies of $^{18}$F-BODIPY-1 (50 µCi/mouse) in normal female nude mice at 3 h after injection of tracer Data are expressed as % ID/g±SD (n=3/group).

The biodistribution of $^{18}$F-BODIPY-1 (50 μCi/mouse) was examined in health nude mice 3 h p.i. As shown in FIG. 5, heart uptake was significantly higher than those in blood, muscle and liver. The relative high kidney uptake further confirmed that the probe was cleared from urinal system. The consistence between biodistribution and microPET quantification fully validated the effectiveness of non-invasive microPET cardiac imaging with $^{18}$F-BODIPY-1.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

TABLE 1

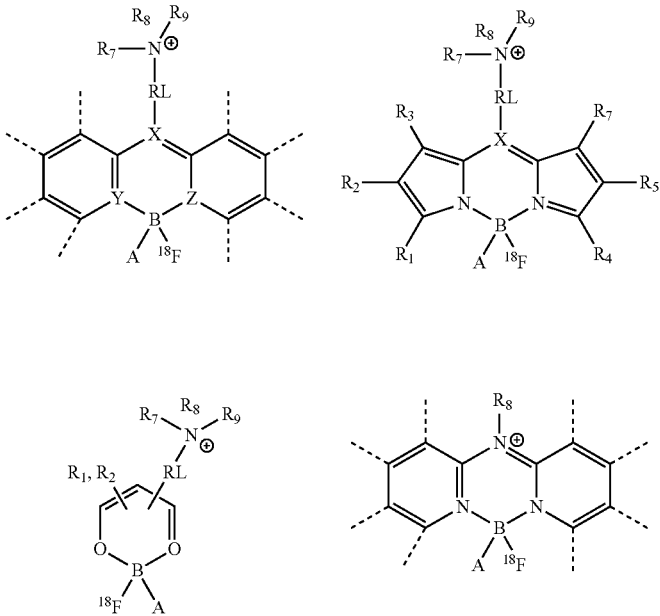

TABLE 1-continued

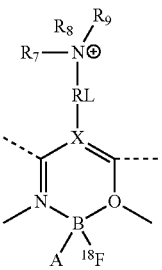

In the above structures, RL is selected from an aliphatic group, an aromatic group, or a PEG linker;
the nitrogen "N" atoms may be replaced with phosphorus "P";
X, Y, and Z are independently selected from C, N, and O;
A and $R_1$-$R_9$ are independently selected from the group consisting of hydrogen, halogen, hydroxy, alkoxy, nitro, substituted and unsubstituted animo, alkyl, cycloalky, carboxy, carboxylic acids and esters thereof, cyano, haloalkyl, aryl, including phenyl and aminophenyl, and heteroaryl.
The RL—$NR_7R_8R_9$ moiety may be in meta or ortho position within the boron-containing ring.

REFERENCES

All publication cited herein, including the foregoing are expressly incorporated herein by references for the purpose of describing and disclosing compositions, preparation kits and methodologies that might be used in connection with the invention:

1. Rischpler C, Park M J, Fung G S, Javadi M, Tsui B M, Higuchi T. Advances in PET myocardial perfusion imaging: F-18 labeled tracers. *Ann Nucl Med.* 2011.
2. Beller G A, Bergmann S R. Myocardial perfusion imaging agents: SPECT and PET. *J Nucl Cardiol.* 2004; 11:71-86.
3. Furer V, Fayad Z A, Mani V, Calcagno C, Farkouh M E, Greenberg J D. Noninvasive Cardiovascular Imaging in Rheumatoid Arthritis: Current Modalities and the Emerging Role of Magnetic Resonance and Positron Emission Tomography Imaging. *Semin Arthritis Rheum.* 2011.
4. Naresh N K, Ben-Mordechai T, Leor J, Epstein F H. Molecular Imaging of Healing After Myocardial Infarction. *Curr Cardiovasc Imaging Rep.* 2011; 4:63-76.
5. Thompson D, Koster M J, Wagner R H, Heroux A, Barron J T. Single photon emission computed tomography myocardial perfusion imaging to detect cardiac allograft vasculopathy. *Eur J Echocardiogr.* 2011.
6. Di Carli M F, Dorbala S, Meserve J, El Fakhri G, Sitek A, Moore S C. Clinical myocardial perfusion PET/CT. *J Nucl Med.* 2007; 48:783-793.
7. Heller G V, Calnon D, Dorbala S. Recent advances in cardiac PET and PET/CT myocardial perfusion imaging. *J Nucl Cardiol.* 2009; 16:962-969.
8. Maddahi J, Czernin J, Lazewatsky J, et al. Phase I, first-in-human study of BMS747158, a novel $^{18}$F-labeled tracer for myocardial perfusion PET: dosimetry, biodistribution, safety, and imaging characteristics after a single injection at rest. *J Nucl Med.* 2011; 52:1490-1498.
9. Nekolla S G, Reder S, Saraste A, et al. Evaluation of the novel myocardial perfusion positron-emission tomography tracer $^{18}$F-BMS-747158-02: comparison to 13N-ammonia and validation with microspheres in a pig model. *Circulation.* 2009; 119:2333-2342.
10. Higuchi T, Fukushima K, Rischpler C, et al. Stable delineation of the ischemic area by the PET perfusion tracer $^{18}$F-fluorobenzyl triphenyl phosphonium after transient coronary occlusion. *J Nucl Med.* 2011; 52:965-969.
11. Madar I, Huang Y, Ravert H, et al. Detection and quantification of the evolution dynamics of apoptosis using the PET voltage sensor $^{18}$F-fluorobenzyl triphenyl phosphonium. *J Nucl Med.* 2009; 50:774-780.
12. Madar I, Ravert H, Dipaula A, Du Y, Dannals R F, Becker L. Assessment of severity of coronary artery stenosis in a canine model using the PET agent $^{18}$F-fluorobenzyl triphenyl phosphonium: comparison with 99mTc-tetrofosmin. *J Nucl Med.* 2007; 48:1021-1030.
13. Wadas T J, Wong E H, Weisman G R, Anderson C J. Copper chelation chemistry and its role in copper radiopharmaceuticals. *Curr Pharm Des.* 2007; 13:3-16.
14. Wallhaus T R, Lacy J, Whang J, Green M A, Nickles R J, Stone C K. Human biodistribution and dosimetry of the PET perfusion agent copper-62-PTSM. *J Nucl Med.* 1998; 39:1958-1964.
15. Gottumukkala V, Heinrich T K, Baker A, et al. Biodistribution and stability studies of [18F]fluoroethylrhodamine B, a potential PET myocardial perfusion agent. *Nucl Med Biol.* 2010; 37:365-370.
16. Li Z, Lin T P, Liu S, et al. Rapid aqueous [18F]-labeling of a bodipy dye for positron emission tomography/fluorescence dual modality imaging. *Chem Commun (Camb).* 2011; 47:9324-9326.
17. Wu Y, Zhang X, Xiong Z, et al. microPET imaging of glioma integrin $a_vb_3$ expression using $^{64}$Cu-labeled tetrameric RGD peptide. *J Nucl Med.* 2005; 46:1707-1718.
18. Li Z B, Cai W, Cao Q, et al. $^{64}$Cu-labeled tetrameric and octameric RGD peptides for small-animal PET of tumor $a_vb_3$ integrin expression. *J Nucl Med.* 2007; 48:1162-1171.
19. Cooper C R, Chay C H, Pienta K J. The role of $a_vb_3$ in prostate cancer progression. *Neoplasia.* 2002; 4:191-194.
20. Zheng D Q, Woodard A S, Tallini G, Languino L R. Substrate specificity of $a_vb_3$ integrin-mediated cell migration and phosphatidylinositol 3-kinase/AKT pathway activation. *J Biol Chem.* 2000; 275:24565-24574.
21. Cai W, Wu Y, Chen K, Cao Q, Tice D A, Chen X. In vitro and In vivo Characterization of [64]Cu-Labeled Abegrin™, a Humanized Monoclonal Antibody against Integrin $a_vb_3$. *Cancer Res.* 2006; 66:9673-9681.
22. Markwalder R, Reubi J C. Gastrin-releasing peptide receptors in the human prostate: relation to neoplastic transformation. *Cancer Res.* 1999; 59:1152-1159.
23. Bybee K A, Lee J, Markiewicz R, et al. Diagnostic and clinical benefit of combined coronary calcium and perfusion assessment in patients undergoing PET/CT myocardial perfusion stress imaging. *J Nucl Cardiol.* 2010; 17:188-196.

24. Slomka P J, Alexanderson E, Jacome R, et al. Comparison of Clinical Tools for Measurements of Regional Stress and Rest Myocardial Blood Flow Assessed with 13N-Ammonia PET/CT. *J Nucl Med.* 2012.

25. Purser S, Moore P R, Swallow S, Gouverneur V. Fluorine in medicinal chemistry. *Chem Soc Rev.* 2008; 37:320-330.

26. Miller P W, Long N J, Vilar R, Gee A D. Synthesis of C-11, F-18, O-15, and N-13 Radiolabels for Positron Emission Tomography. *Angew Chem Int Ed.* 2008; 47:8998-9033.

27. Dolle F, Roeda D, Kuhnast B, Lasne M-C. Fluorine-18 chemistry for molecular imaging with positron emission tomography. *Fluorine and Health.* 20083-65.

28. Loudet A, Burgess K. BODIPY dyes and their derivatives: Syntheses and spectroscopic properties. *Chem Rev.* 2007; 107:4891-4932.

29. Ulrich G, Ziessel R, Harriman A. The chemistry of fluorescent Bodipy dyes: versatility unsurpassed. *Angew Chem Int Ed.* 2008; 47:1184-1201.

30. Flewelling R F, Hubbell W L. Hydrophobic ion interactions with membranes. Thermodynamic analysis of tetraphenylphosphonium binding to vesicles. *Biophys J.* 1986; 49:531-540.

31. Ross M F, Kelso G F, Blaikie F H, et al. Lipophilic triphenylphosphonium cations as tools in mitochondrial bioenergetics and free radical biology. *Biochemistry (Mosc).* 2005; 70:222-230.

What is claimed is:

1. A cardiac imaging agent comprising:
   a dual mode imaging tracer capable of acting both as a fluorescent tracer and a positron emission tomography tracer, wherein said dual mode imaging tracer comprises a fluorescent core with a boron-flouride element embedded therein, and wherein the tracer has one of the following general formulae:

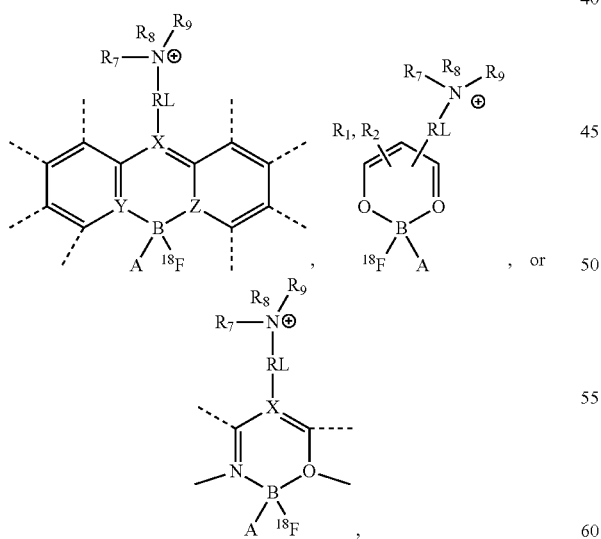

wherein

RL is selected from an aliphatic group being a $C_1$-$C_{10}$ straight or branched chain alkyl or cycloalkyl, an aromatic group being a monocyclic or condensed ring aromatic hydrocarbon, or a PEG linker;

X is C, and Y and Z are independently selected from C, N, and O;

A, $R_1$-$R_2$ and $R_7$-$R_9$ are independently selected from the group consisting of hydrogen, halogen, hydroxy, alkoxy, nitro, substituted and unsubstituted animo, alkyl, cycloalkyl, carboxy, carboxylic acids and esters thereof, cyano, haloalkyl, aryl, including phenyl and aminophenyl, and heteroaryl.

2. The cardiac imaging agent of claim 1, wherein the tracer has the following general formulae:

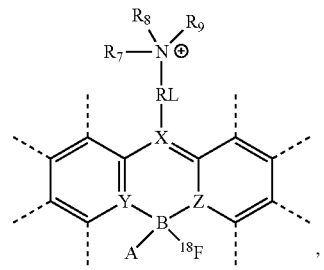

wherein

RL is as recited in claim 1;

X is C, and Y and Z are independently selected from C, N, and O;

A and $R_7$-$R_9$ are independently selected from the group consisting of hydrogen, halogen, hydroxy, alkoxy, nitro, substituted and unsubstituted animo, alkyl, cycloalkyl, carboxy, carboxylic acids and esters thereof, cyano, haloalkyl, aryl, including phenyl and aminophenyl, and heteroaryl.

3. The cardiac imaging agent of claim 1, wherein the tracer has the following general formulae:

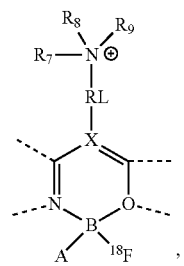

wherein

RL is as recited in claim 1;

X is C;

A and $R_7$-$R_9$ are independently selected from the group consisting of hydrogen, halogen, hydroxy, alkoxy, nitro, substituted and unsubstituted animo, alkyl, cycloalkyl, carboxy, carboxylic acids and esters thereof, cyano, haloalkyl, aryl, including phenyl and aminophenyl, and heteroaryl.

4. The cardiac imaging agent of claim 1, wherein the tracer has the following general formulae:

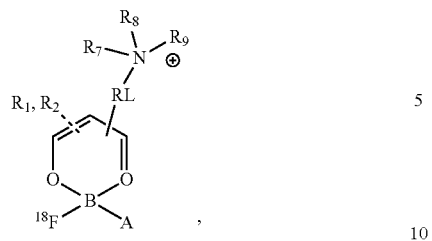
wherein
RL is as recited in claim 1;
A, $R_1$-$R_2$ and $R_7$-$R_9$ are independently selected from the group consisting of hydrogen, halogen, hydroxy, alkoxy, nitro, substituted and unsubstituted animo, alkyl, cycloalkyl, carboxy, carboxylic acids and esters thereof, cyano, haloalkyl, aryl, including phenyl and aminophenyl, and heteroaryl.
* * * * *